(12) United States Patent
Satozono

(10) Patent No.: US 10,330,590 B2
(45) Date of Patent: Jun. 25, 2019

(54) CIRCULAR DICHROISM MEASURING METHOD AND CIRCULAR DICHROISM MEASURING DEVICE

(71) Applicant: HAMAMATSU PHOTONICS K.K., Hamamatsu-shi, Shizuoka (JP)

(72) Inventor: Hiroshi Satozono, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/315,433

(22) PCT Filed: May 18, 2015

(86) PCT No.: PCT/JP2015/064205
§ 371 (c)(1),
(2) Date: Dec. 1, 2016

(87) PCT Pub. No.: WO2015/186500
PCT Pub. Date: Dec. 10, 2015

(65) Prior Publication Data
US 2017/0191928 A1    Jul. 6, 2017

(30) Foreign Application Priority Data

Jun. 2, 2014  (JP) ................................. 2014-114061

(51) Int. Cl.
*G01J 4/04* (2006.01)
*G01N 21/19* (2006.01)
*G01N 21/21* (2006.01)

(52) U.S. Cl.
CPC ................ *G01N 21/19* (2013.01); *G01J 4/04* (2013.01); *G01N 2021/216* (2013.01)

(58) Field of Classification Search
CPC ........ G01N 21/19; G01N 21/21; G01N 21/23; G01N 2021/216; G01N 2021/217;
(Continued)

(56) References Cited

U.S. PATENT DOCUMENTS 3,540,827 A * 11/1970 Badoz ................... G01N 21/19
                                                      250/225
5,298,973 A *  3/1994 Fukazawa .............. G02B 26/06
                                                      250/225
(Continued)

FOREIGN PATENT DOCUMENTS

JP      H6-317518      11/1994
JP      3341928 B2     11/2002
(Continued)

OTHER PUBLICATIONS

Chao, Y.F. et al., "Artifactual circular dichroism effect in a photoelastic modulator," 2010, Optics Communications, 283, pp. 4582-4585.*
(Continued)

*Primary Examiner* — Gordon J Stock, Jr.
(74) *Attorney, Agent, or Firm* — Drinker Biddle & Reath LLP

(57) ABSTRACT

Circular dichroism can be accurately measured even when a phase modulation element with a distortion component is used.

A circular dichroism measuring method using a circular dichroism measuring device 2 includes a step of measuring Ip(t) (S101: phase amount change acquisition step), a step of measuring Is(t) (S102: sample data acquisition step), a step of converting Ip(t) to δ(t) (S103: phase amount change acquisition step), a step of converting Is(t) to Is(δ) (S104: analysis step/Is(δ) calculation step), and a step of performing curve fitting to calculate matrix elements S00, S02, and S03 (S105: analysis step/matrix element calculation step).

2 Claims, 14 Drawing Sheets

(58) Field of Classification Search
CPC ........ G01N 2021/218; G01J 4/00; G01J 4/02; G01J 4/04; G01J 2004/001; G01J 2004/002; G01J 2004/004; G01J 2004/005; G01J 2004/007; G01J 2004/008; G01J 3/42; G01J 3/433; G02F 1/0128; G02F 1/131
USPC .................................................. 356/364–370
See application file for complete search history.

(56) References Cited

U.S. PATENT DOCUMENTS

| | | | |
|---|---|---|---|
| 6,060,710 | A | 5/2000 | Carrieri et al. |
| 9,036,151 | B2 * | 5/2015 | Lo .............................. G01J 4/04 356/364 |
| 2011/0026026 | A1 | 2/2011 | Jez et al. |
| 2013/0308132 | A1 | 11/2013 | Giakos |

FOREIGN PATENT DOCUMENTS

| | | | |
|---|---|---|---|
| JP | 2012202812 A | * | 10/2012 |
| JP | 2013-217702 A | | 10/2013 |
| JP | 2013231707 A | * | 11/2013 |

OTHER PUBLICATIONS

DiNitto, Julie M. et al., "Modeling, Characterizing, and Accommodating Static Birefringence in Circular and Linear Dichroism Spectroscopy," 2013, Applied Spectroscopy, vol. 67, No. 10, pp. 1200-1204.*
DiNitto, Julie M. et al., "Novel Technique for Improvement in Calibration of the Photoelastic Modulator in Circular and Linear Dichroism Spectroscopy," 2013, Applied Spectroscopy, vol. 67, No. 1, pp. 40-48.*
Satozono, Hiroshi, "Elimination of artifacts derived from the residual birefringence of a phase modulator for circular dichroism by retardation domain analysis," 2015, Optics Letters, vol. 40, No. 7, pp. 1161-1164.*
Y. Shindo et al., "Circular dichroism measurements. I. Calibration of a circular dichroism spectrometer", Review of Scientific Instruments, 1985, p. 32-p. 39.
Y. Shindo, "On the Measurements of Circular Dichroism I. Software and Hardware of the Spectrometer", Journal of SPSJ, 1985, vol. 34, No. 3, p. 153-p. 161.
Y. Shindo et al., "On the Problems of CD Spectropolarimeters. II: Artifacts in CD Spectrometers", Applied Spectroscopy, 1985, vol. 39, No. 5, p. 860-p. 868.
International Preliminary Report on Patentability dated Dec. 15, 2016 for PCT/JP2015/064205.

* cited by examiner

US 10,330,590 B2

CIRCULAR DICHROISM MEASURING METHOD AND CIRCULAR DICHROISM MEASURING DEVICE

TECHNICAL FIELD

The present invention relates to a circular dichroism measuring method and a circular dichroism measuring device.

BACKGROUND ART

Circular dichroism (CD) is a phenomenon caused by optical activity (chirality) of molecules and is defined as a difference in absorbance with respect to left and right circularly polarized light. Since spectral information of this circular dichroism reflects a high-order structure of molecules, circular dichroism is particularly suitably applied to, for example, analysis of a high order structure of biologically active substance. For this circular dichroism, a method of irradiating a sample with left and right circularly polarized lights and obtaining a difference in absorbance from an intensity difference of transmitted light is generally used.

In measurement of the circular dichroism, measurement using a so-called modulation method is generally used. In a modulation method, an optical phase modulator such as a photoelastic modulator or a Pockel cell is used as a circular polarization modulator that generates circularly polarized light. However, modulation of the circular polarization modulator in which there is a distortion component is known (see, for example, Patent Literature 1 and Non Patent Literature 1).

CITATION LIST

Patent Literature

[Patent Literature 1] Japanese Patent No. 3341928

Non Patent Literature

[Non Patent Literature 1] Shinto, Spectroscopy Study, Vol. 34, No. 3, page 153 (1985)

SUMMARY OF INVENTION

Technical Problem

In recent years, various studies have been performed in order to manufacture a circular dichroism measuring device at a lower cost. However, an inexpensive phase modulation element in which there is a distortion component cannot be applied as a phase modulation element (circular polarization modulator) constituting the circular dichroism measuring device, and there is a problem of achievement of a low cost.

The present invention has been made in view of the above circumstances, and relates to a circular dichroism measuring method and a circular dichroism measuring device capable of accurately measuring circular dichroism even when a phase modulation element with a distortion component is used.

Solution to Problem

To achieve the above object, a circular dichroism measuring method according to an aspect of the present invention is a circular dichroism measuring method in a circular dichroism measuring device including a light source, a polarization plate that extracts linearly polarized light from light emitted from the light source, a phase modulation element that modulates the linearly polarized light, and a light detector that detects light modulated by the phase modulation element and then transmitted through a sample, the circular dichroism measuring method including: a sample data acquisition step of acquiring a change in a light intensity with respect to time in the light detector; a phase amount change acquisition step of acquiring a change in a phase amount with respect to time of the phase modulation element; and an analysis step of converting the change in light intensity acquired in the sample data acquisition step into a change with respect to the phase amount on the basis of the change in the phase amount acquired in the phase amount change acquisition step, and calculating matrix elements S00, S02, and S03 when a Mueller matrix according to the sample is as shown in Equation (1) below on the basis of the change.

[Math. 1]

$$S = S(\theta) = e^{-Av} \cdot \begin{pmatrix} S00 & S01 & S02 & S03 \\ S10 & S11 & S12 & S13 \\ S20 & S21 & S22 & S23 \\ S30 & S31 & S32 & S33 \end{pmatrix} \quad (1)$$

According to the circular dichroism measuring method, a temporal change in a phase amount in the phase modulation element is acquired, the change in light intensity acquired in the sample data acquisition step is converted into a change with respect to the phase amount on the basis of the change, and then, matrix elements in the Mueller matrix are calculated. Since the matrix elements in the Mueller matrix are calculated in consideration of the temporal change of the phase amount of the phase modulation element, when the phase modulation element has a distortion component, the matrix elements can be calculated in consideration of this. Thus, it is possible to accurately measure the circular dichroism.

Here, the phase amount change acquisition step includes acquiring data Is(t) indicating a temporal change in a light signal detected by the light detector by emitting light from the light source in a state in which the sample is disposed, and the phase amount change acquisition step includes: a step of acquiring data Ip(t) indicating a temporal change in a light signal detected in the light detector by emitting light from the light source in a state in which a second polarization plate having a relationship with the polarization plate giving crossed Nicols is disposed on an optical path from the light source, in place of the sample; and a step of converting the data Ip(t) into data δ(t) indicating a temporal change of the phase change amount due to the phase modulation element using Equation (2) below,

[Math. 2]

$$\delta(t) = \cos^{-1}\left(1 - \frac{2I_P(t)}{I_m}\right) \quad (2)$$

and the analysis step includes an Is(δ) calculation step of calculating data Is(δ) according to the phase amount at time t of data Is(t) of the sample on the basis of the data δ(t) of the phase change amount; and a matrix element calculation step of performing fitting on the data Is(δ) using Equation (3) below to calculate matrix elements S00, S02, and S03 in a Mueller matrix according to the sample.

[Math. 3]

$$I = \frac{1}{2}e^{-Av} \cdot (S00 + S03\cos\delta - S02\sin\delta) \quad (3)$$

As described above, it is possible to perform circular dichroism measurement in consideration of a temporal change of the phase change amount by calculating the data Is(δ) according to the phase amount at time t of the data Is(t) of the sample on the basis of the data δ(t) of the phase change amount, and performing fitting on the data Is(δ) to calculate matrix elements S00, S02, and S03 in a Mueller matrix according to the sample.

The invention of the above circular dichroism measuring method can be described as an invention of a circular dichroism measuring device as follows.

That is, a circular dichroism measuring device according to an aspect of the present invention is a circular dichroism measuring device including a light source, a polarization plate that extracts linearly polarized light from light emitted from the light source, a phase modulation element that modulates the linearly polarized light, and a light detector that detects light modulated by the phase modulation element and then transmitted through a sample, the circular dichroism measuring device including: a sample data acquisition means for acquiring a change in a light intensity with respect to time in the light detector; a phase amount change acquisition means for acquiring a change in a phase amount with respect to time of the phase modulation element; and an analysis means for converting the change in light intensity acquired in the sample data acquisition means into a change with respect to the phase amount on the basis of the change in the phase amount acquired in the phase amount change acquisition means, and calculating matrix elements S00, S02, and S03 when a Mueller matrix according to the sample is as shown in Equation (4) below on the basis of the change.

[Math. 4]

$$S = S(\theta) = e^{-Av} \cdot \begin{pmatrix} S00 & S01 & S02 & S03 \\ S10 & S11 & S12 & S13 \\ S20 & S21 & S22 & S23 \\ S30 & S31 & S32 & S33 \end{pmatrix}. \quad (4)$$

Further, the phase amount change acquisition means acquires data Is(t) indicating a temporal change in a light signal detected in the light detector by emitting light from the light source in a state in which the sample is disposed, and the phase amount change acquisition means includes: an Ip(t) acquisition means for acquiring data Ip(t) indicating a temporal change in a light signal detected in the light detector by emitting light from the light source in a state in which a second polarization plate having a relationship with the polarization plate giving crossed Nicols is disposed on an optical path from the light source, in place of the sample; and a conversion means for converting the data Ip(t) into data δ(t) indicating a temporal change of the phase change amount due to the phase modulation element using Equation (5) below,

[Math. 5]

$$\delta(t) = \cos^{-1}\left(1 - \frac{2I_P(t)}{I_m}\right) \quad (5)$$

and the analysis means includes an Is(δ) calculation means for calculating data Is(δ) according to the phase amount at time t of data Is(t) of the sample on the basis of the data δ(t) of the phase change amount; and a matrix element calculation means for performing fitting on the data Is(δ) using Equation (6) below to calculate matrix elements S00, S02, and S03 in a Mueller matrix according to the sample.

[Math. 6]

$$I = \frac{1}{2}e^{-Av} \cdot (S00 + S03\cos\delta - S02\sin\delta) \quad (6)$$

Further, the circular dichroism measuring device according to an aspect of the present invention further includes a beam splitter that splits the light emitted from the phase modulation element in two, and a light detector constituting the sample data acquisition means and detecting light transmitted through the sample is formed on an optical path for one of the two lights split by the beam splitter, and the second polarization plate constituting the Ip(t) acquisition means and the second light detector detecting light transmitted through the second polarization plate are formed on an optical path for the other of the two lights split by the beam splitter.

In such a circular dichroism measuring device, since it is possible to simultaneously realize the sample data acquisition means and the Ip(t) acquisition means by forming two optical paths using the beam splitter, it is possible to acquire a phase change of the phase modulation element in real time. Thus, for example, even when a phase modulation element with significant temperature characteristics or drift characteristics, such as a liquid crystal phase modulation element, is used, it is possible to perform high-accuracy circular dichroism measurement.

Advantageous Effects of Invention

According to the present invention, the circular dichroism measuring method and the circular dichroism measuring device capable of accurately measuring circular dichroism even when a phase modulation element with a distortion component is used are provided.

DESCRIPTION OF EMBODIMENTS

Figure 1:
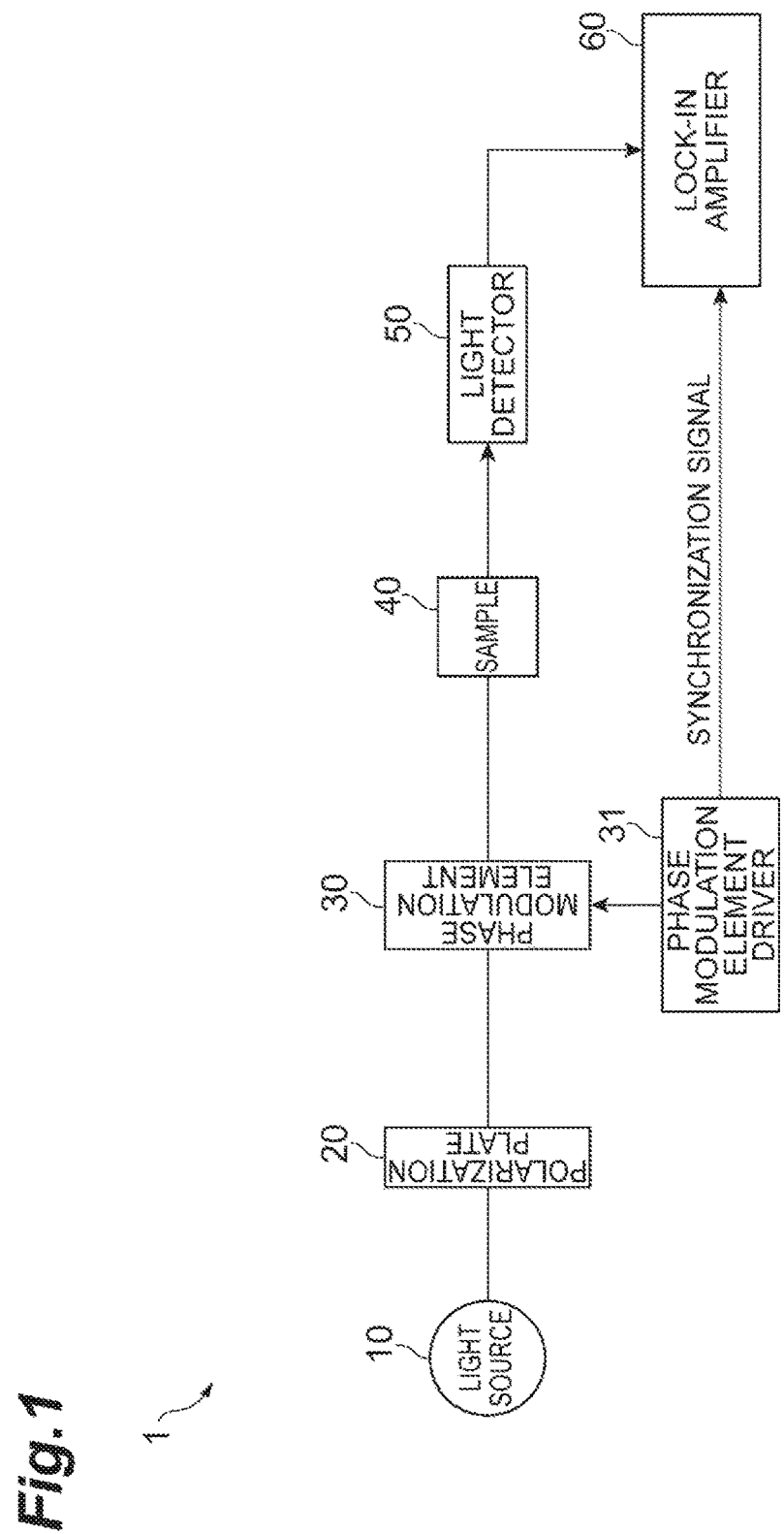
FIG. 1 is a diagram illustrating a schematic configuration of a circular dichroism measuring device of the related art.

Hereinafter, embodiments of the present invention will be described in detail with reference to the accompanying drawings. The same elements are denoted with the same reference numerals in description of the drawings, and repeated description will be omitted.

(First Embodiment)

In the following description, schematic description of a configuration of a circular dichroism measuring device of the related art and circular dichroism thereof will be described and then a circular dichroism measuring device and a circular dichroism measuring method according to the first embodiment will be described. In the following description, a traveling direction of light from a light source is a Z-axis, and two axes perpendicular and orthogonal to the Z-axis are an X-axis (vertical direction) and a Y-axis (horizontal direction).

FIG. 1 is a schematic configuration diagram of a circular dichroism measuring device of the related art. As illustrated in FIG. 1, in the circular dichroism measuring device, a light source 10, a polarization plate 20, a phase modulation element 30, and a light detector 50 are arranged in this order, and a sample 40 is arranged between the phase modulation element 30 and the light detector. Further, the modulation of the phase modulation element 30 is controlled by a phase modulation element driver 31, and a synchronization signal from the phase modulation element driver 31 is sent to a lock-in amplifier 60 connected to the light detector 50.

The light source 10 emits light for irradiating the sample. The light emitted from the light source 10 is unpolarized light. For example, a deuterium lamp that emits light with a wavelength of 280 nm is used as the light source 10.

The light emitted from the light source 10 is incident on the polarization plate 20. In the polarization plate 20, linearly polarized light is extracted from the light emitted from the light source 10. For example, a Glan-Taylor prism is used as the polarization plate 20. Here, the polarization plate 20 is assumed to extract linearly polarized light in a direction of 0° with respect to an X-axis. A filter for removing a wavelength component, a noise component, or the like unnecessary for circular dichroism measurement may be provided at a preceding stage with respect to the polarization plate 20.

The linearly polarized light extracted by the polarization plate 20 is converted into right circularly polarized light or left circularly polarized light by a circular polarization modulator and emitted. The phase modulation element 30 (phase modulation means) and the phase modulation element driver 31 as a phase modulation signal oscillator are included. The phase modulation element 30 has an optical axis in a direction of 45° around the Z-axis with respect to the X-axis. The phase modulation element driver 31 periodically alternately oscillates a signal for instructing conversion to the right circularly polarized light and a signal for instructing conversion to the left circularly polarized light, as a modulation signal. The phase modulation element driver 31 oscillates, for example, a modulation signal with a period of 50 kHz. The linearly polarized light incident on the phase modulation element 30 is modulated on the basis of the modulation signal oscillated by the phase modulation element driver 31 so that a phase difference between two orthogonal polarized light components periodically changes, to be alternately converted into the right or left circularly polarized light and emitted. For example, a photoelastic modulator or a Pockel cell may be used as a specific element for the phase modulation element 30.

Further, the modulation signal generated by the phase modulation element driver 31 is sent from the phase modulation element driver 31 to the lock-in amplifier 60, as a synchronization signal. In the lock-in amplifier 60, the intensity of the light detected by the light detector 50 and the modulation signal from the phase modulation element driver 31 are combined such that the measurement of the circular dichroism is performed.

Here, a specific method of calculating the circular dichroism will be described. The circular dichroism is defined as a difference between absorbance $A_L$ with respect to the left circularly polarized light and absorbance $A_R$ with respect to the right circularly polarized light. The measurement of the circular dichroism is realized by irradiating the sample with the left and right circularly polarized lights according to this definition and obtaining a difference between the absorbances from the intensity of transmitted light. This measuring method is expressed in a Mueller matrix method as follows. First, a Mueller matrix according to the sample is expressed by Equation (11) below. Here, $A_v$ is an average absorbance of the sample.

[Math. 7]

$$S = S(\theta) = e^{-Av} \cdot \begin{pmatrix} S00 & S01 & S02 & S03 \\ S10 & S11 & S12 & S13 \\ S20 & S21 & S22 & S23 \\ S30 & S31 & S32 & S33 \end{pmatrix} \quad (11)$$

According to the Mueller matrix method, if the left circularly polarized light is transmitted through the sample, an intensity of the transmitted light is expressed by Equation (12) below.

[Math. 8]

$$e^{-Av} \cdot \begin{pmatrix} S00 & S01 & S02 & S03 \\ S10 & S11 & S12 & S13 \\ S20 & S21 & S22 & S23 \\ S30 & S31 & S32 & S33 \end{pmatrix} \begin{pmatrix} 1 \\ 0 \\ -1 \\ 0 \end{pmatrix} = e^{-Av} \cdot \begin{pmatrix} S00 - S02 \\ S10 - S12 \\ S20 - S22 \\ S30 - S32 \end{pmatrix} \quad (12)$$

That is, the light intensity obtained as an output is $e^{-Av} \cdot (S00-S02)$. Since an incident light intensity is 1, the absorbance $A_L$ is calculated as in Equation (13) below.

[Math. 9]

$$A_L = -\log[e^{-Av} \cdot (S00-S02)] \quad (13)$$

Similarly, if the right circularly polarized light is transmitted through the sample, the intensity of the transmitted light is expressed by Equation (14) below.

[Math. 10]

$$e^{-Av} \cdot \begin{pmatrix} S00 & S01 & S02 & S03 \\ S10 & S11 & S12 & S13 \\ S20 & S21 & S22 & S23 \\ S30 & S31 & S32 & S33 \end{pmatrix} \begin{pmatrix} 1 \\ 0 \\ 1 \\ 0 \end{pmatrix} = e^{-Av} \cdot \begin{pmatrix} S00 + S02 \\ S10 + S12 \\ S20 + S22 \\ S30 + S32 \end{pmatrix} \quad (14)$$

That is, the light intensity obtained as an output is $e^{-Av} \cdot (S00+S02)$. Since the incident light intensity is 1, the absorbance $A_R$ is calculated as in Equation (15) below.

[Math. 11]

$$A_R = -\log[e^{-Av} \cdot (S00+S02)] \quad (15)$$

Since the circular dichroism is calculated from a difference between the left and right circularly polarized lights, a difference between $A_L$ and $A_R$ is obtained as in Equation (16) below.

[Math. 12]

$$\begin{aligned} A_L - A_R &= -\log[e^{-Av} \cdot (S00-S02)] + \log[e^{-Av} \cdot (S00+S02)] \quad (16) \\ &= \log\left[\frac{e^{-Av} \cdot (S00+S02)}{e^{-Av} \cdot (S00-S02)}\right] = -\log\left[\frac{S00-S02}{S00+S02}\right] \\ &= -\log\left[1 + \frac{-S02}{S00+S02}\right] \end{aligned}$$

Here, since a value of S02 is usually very small compared to S00, a fraction in Equation (16) is very small compared to 1. Since, generally, x is sufficiently smaller than 1 and $\log(1+x)$ approximates to x, if this is applied to Equation (16), the difference between the left and right circularly polarized lights can be finally expressed as in Equation (17).

[Math. 13]

$$\begin{aligned} A_L - A_R &= -\log\left[1 + \frac{-S02}{S00+S02}\right] \quad (17) \\ &\approx \frac{-S02}{S00+S02} \approx \frac{S02}{S00} \end{aligned}$$

That is, measurement of the circular dichroism as in the definition corresponds to obtaining a ratio of S02 to S00 in the Mueller matrix according to the sample.

Here, the light intensity detected by the light detector 50 of the circular dichroism measuring device 1 of FIG. 1 is expressed by Equation (18) using a Mueller matrix method.

[Math. 14]

$$I = \frac{1}{2} e^{-Av} \cdot (S00 + S03\cos\delta - S02\sin\delta) \quad (18)$$

Here, $\delta$ is a phase change amount of the phase modulation element, and temporally varies as shown in Equation (19) below.

[Math. 15]

$$\delta = \delta_0 \sin(\omega t + \alpha) \quad (19)$$

Here, $\omega$ denotes a modulation angular frequency ($=2\pi f$: f is a modulation frequency) of the phase modulation element 30, $\delta_0$ denotes a maximum delay amount of the phase modulation element 30, and $\alpha$ denotes residual distortion of the phase modulation element 30, linearly polarized light birefringence derived from the an optical component, or both of them.

Here, when the circular dichroism measuring device has an ideal configuration, that is, when the phase modulation element 30 has no distortion component and linearly polarized light birefringence due to optical components including others does not occur, $\alpha=0$. Accordingly, Equation (18) above can be developed as Equation (20). Here, $J_x$ is an x-order Bessel function.

[Math. 16]

$$\begin{aligned} I = \frac{1}{2} e^{-Av}[&S00 + S03 \cdot J_0(\delta_0) + \quad (20) \\ &S03 \cdot 2J_2(\delta_0)\cos(2\omega t) + \ldots - S02 \cdot 2J_1(\delta_0)\sin(\omega t) - \ldots ] \end{aligned}$$

According to Equation (20), S02 appears as a frequency $\omega$ component. Further, in Equation (20), S03 appears as a $2\omega$ component. Thus, the S02 component and the S03 component can be measured individually by separating S02 and S03 using the lock-in amplifier or the like.

However, the above is a case in which the circular dichroism measuring device has an ideal configuration, and when a is not zero, that is, when there is residual distortion in the phase modulation element 30 or there is linear polarization birefringence in an optical component, Equation (18) is developed as in Equation (21) below.

[Math. 17]

$$\begin{aligned} I = \frac{1}{2}e^{-Av}[&S00 + S03 \cdot \cos\alpha \cdot J_0(\delta_0) + S03 \cdot \cos\alpha \cdot 2J_2(\delta_0)\cos(2\omega t) \quad (21) \\ &-S03 \cdot \sin\alpha \cdot 2J_1(\delta_0)\sin(\omega t) + \ldots - S02 \cdot \sin\alpha \cdot J_0(\delta_0) - \\ &S02 \cdot \cos\alpha \cdot 2J_1(\delta_0)\sin(\omega t) \underline{+ S02 \cdot \sin\alpha \cdot 2J_2(\delta_0)\cos(2\omega t)} + \ldots ] \end{aligned}$$

In Equation (21), it is shown that S03 is incorporated into a frequency a component and S02 is incorporated into a $2\omega$ component with a weight of sin a due to residual distortion $\alpha$, as indicated by an underline in Equation (21), that is, it is not possible to separate S02 and S03 through the analysis in a frequency domain of a lock-in amplifier or the like.

S03 is for linear dichroism (LD) according to a general equation of the Mueller matrix of an optically active sample.

In a liquid sample in which S03=LD=0 is satisfied, the above problem does not occur. However, in a solid, gel, or film-like sample, there is not little LD, and a problem occurs in that this LD is incorporated into a CD signal as an artifact component.

Therefore, in CD measurement of the related art, since a phase modulation element with less residual distortion is required and adoption of a high-accuracy phase modulation element such as a photoelastic modulator (PEM) is essential, the entire circular dichroism measuring device has been inevitably expensive.

On the other hand, in the circular dichroism measuring method using the circular dichroism measuring device according to this embodiment, it is possible to separate S02 and S03 in the Mueller matrix even when the phase modulation element includes a distortion component by separately measuring the phase change amount with respect to time of the phase modulation element.

Figure 2:
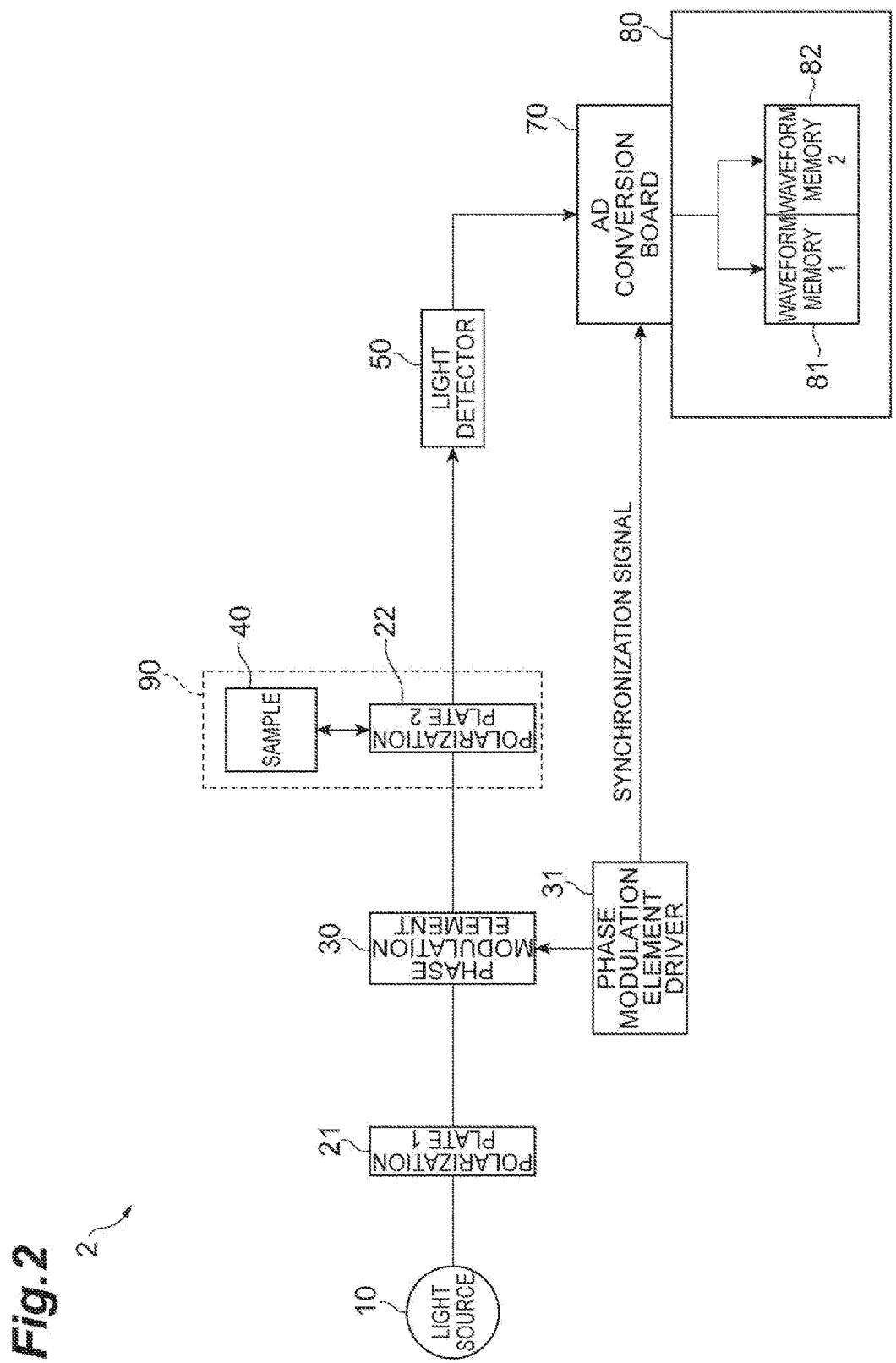
FIG. 2 is a diagram illustrating a schematic configuration of a circular dichroism measuring device according to a first embodiment.

FIG. 2 illustrates a configuration of the circular dichroism measuring device 2 according to the first embodiment. As illustrated in FIG. 2, the circular dichroism measuring device 2 includes a light source 10, a first polarization plate 21 (polarization plate 1), a phase modulation element 30, a phase modulation element driver 31, a second polarization plate 22 (polarization plate 2), a light detector 50, an AD conversion board 70, and a computer 80. The second polarization plate 22 and the sample 40 are held by an exchange mechanism 90 capable of exchanging an object disposed on the optical path for the light from the light source 10, and either of the second polarization plate 22 and the sample 40 is disposed on the optical path. The first polarization plate 21 is assumed to extract linearly polarized light in a direction of 0° with respect to the X-axis, similar to the polarization plate 20. Further, the phase modulation element 30 is similarly set in a direction of 45° around the Z-axis with respect to the X-axis. Further, it is assumed that the direction of the second polarization plate 22 is changed for each measurement, and linearly polarized light in the changed direction is extracted.

In the above circular dichroism measuring device 2, the light from the light source 10 is converted into linearly polarized light in the X-axis direction by the first polarization plate 21 and phase-modulated by the phase modulation element 30 set in a direction of 45° around the Z-axis with respect to the X-axis, and modulated light including right and left circularly polarized lights is generated. In the circular dichroism measuring device 2 according to this embodiment, a PEM-100/ICF50 model which is a photoelastic modulator (PEM) available from Hinds Instruments can be used as the phase modulation element 30. A material of the photoelastic modulator (PEM) is CaF2. The phase modulation element 30 is driven by the phase modulation element driver 31, similar to the circular dichroism measuring device 1. A synchronization signal for modulation is simultaneously output from the phase modulation element driver 31. A modulation frequency may be, for example, 50 kHz.

Figure 3:
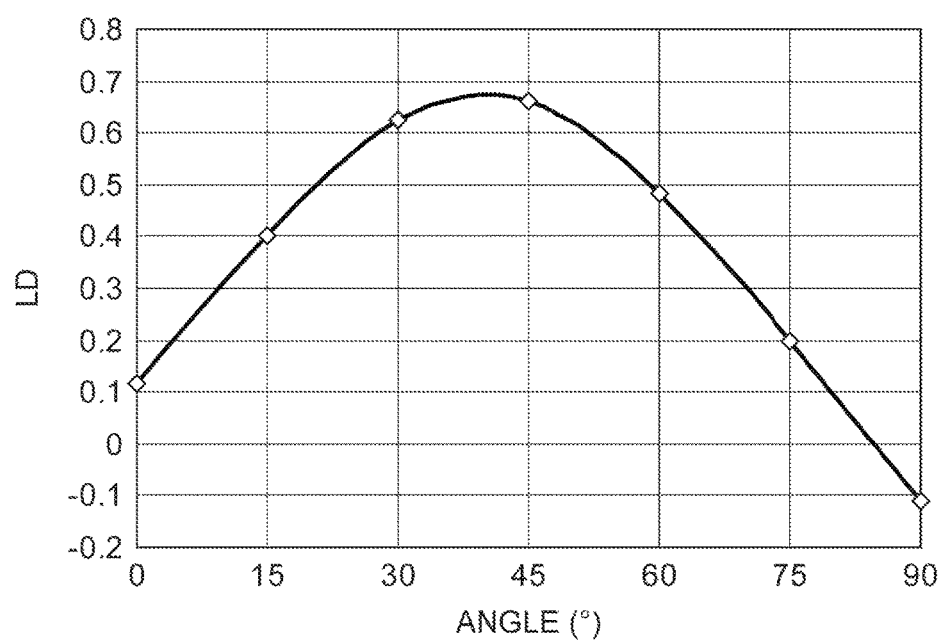
FIG. 3 is a diagram illustrating linear dichroism (LD) of a sample.

The modulated light generated by the phase modulation element 30 is transmitted through the sample 40 or the second polarization plate 22 held by the exchange mechanism 90, and is detected by the light detector 50. A configuration in which exchange of the sample 40 and the second polarization plate 22 is manually performed may be adopted in place of the configuration in which the exchange mechanism 90 is used. In the following embodiments, a case in which a sample obtained by extending a polyvinyl alcohol film stained with Congo Red dye is used as the sample 40 will be described. The polyvinyl alcohol film stained with Congo Red dye has a large linear dichroism (LD), as illustrated in FIG. 3.

A signal according to the light detected in the light detector 50 is converted into digital data by the AD conversion board 70 inserted into the computer 80, and then, stored in a first waveform memory 81 (waveform memory 1) or a second waveform memory 82 (waveform memory 2) inside the computer 80. A timing of the start of AD conversion in the AD conversion board 70 is determined on the basis of the synchronization signal that is transmitted from the phase modulation element driver 31.

In the circular dichroism measuring device 2, the light source 10, the first polarization plate 21, the phase modulation element 30, and the light detector 50 function as an Is(t) acquisition means (sample data acquisition means) that acquires data Is(t) indicating a temporal change in a light signal transmitted through the sample. Further, the light source 10, the first polarization plate 21, the second polarization plate 22, the phase modulation element 30, and the light detector 50 function as an Ip(t) acquisition means (phase amount change acquisition means) that acquires data Ip(t) indicating a temporal change in the light signal due to the phase modulation element. Further, the computer 80 functions as conversion means (analysis means) for converting the data Ip(t) into data δ(t) indicating the temporal change in the phase change amount due to the phase modulation element, an Is(δ) calculation means (analysis means) for calculating the data Is(δ) according to the phase amount at time t of the data Is(t) of the sample on the basis of the data δ(t) of the phase change amount, and a matrix element calculation means (analysis means) for performing fitting on the data Is(δ) and calculating matrix elements S00, S02, and S03 in a Mueller matrix according to the sample.

Figure 4:
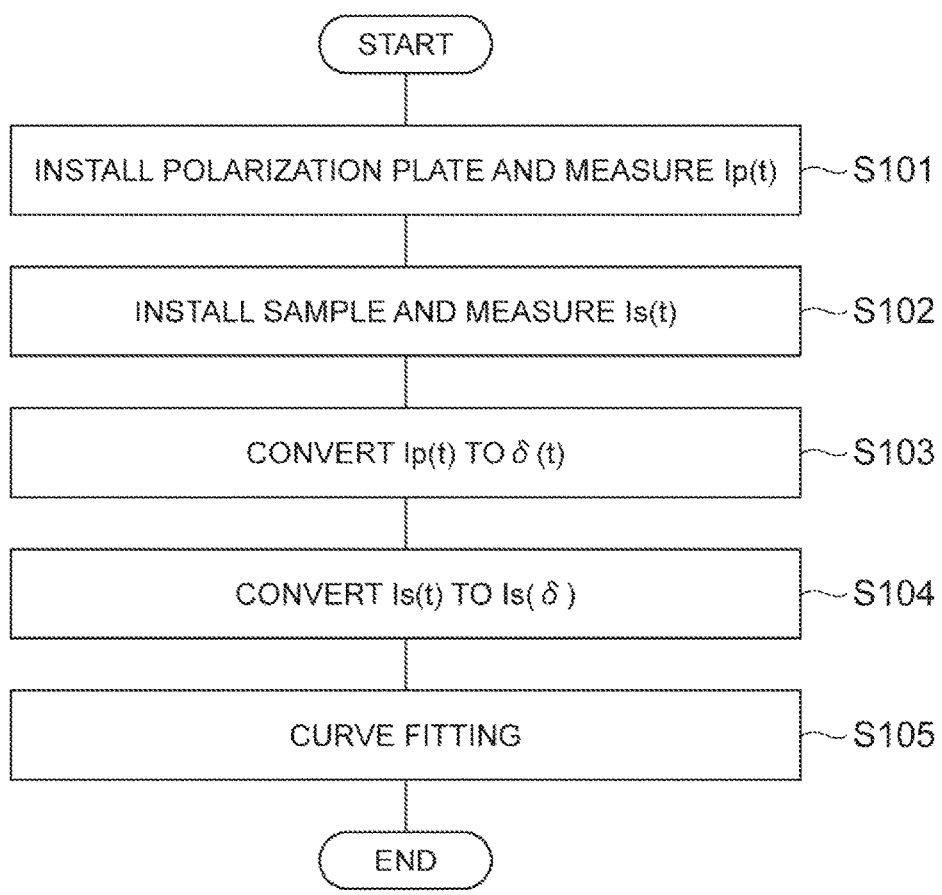
FIG. 4 is a flow diagram illustrating a circular dichroism measuring method.

Further, the circular dichroism measuring method using the circular dichroism measuring device 2 includes steps illustrated in FIG. 4. That is, a step of measuring Ip(t) (S101: phase amount change acquisition step), a step of measuring Is(t) (S102: sample data acquisition step), a step of converting Ip(t) to δ(t) (S103: phase amount change acquisition step), a step of converting Is(t) to Is(δ) (S104: analysis step/Is(δ) calculation step), and a step of performing curve fitting to calculate the matrix elements S00, S02, and S03 (S105: analysis step/matrix element calculation step).

An order of the above steps may be appropriately changed. In particular, there is no problem even when an order of the step of measuring Ip(t) (S101) and the step of measuring Is(t) (S102) is switched, and the step of converting Ip(t) to δ(t) (S103) may be performed after the step of measuring Ip(t) (S101). It is necessary for the step of converting Is(t) to Is(δ) (S104) to be performed after all of preceding steps (S101 to S103) end. The step of performing curve fitting (S105) is performed after the step of converting Is(t) to Is(δ) (S104).

First, the second polarization plate 22 is disposed in the optical path. The second polarization plate 22 is disposed so that the polarization axis has a relationship with the X-axis direction, that is, the first polarization plate 21 giving parallel Nicols. In this state, measurement light is emitted from the light source 10, and a light signal intensity obtained without driving the phase modulation element 30 is recorded. This intensity is referred to as Im.

Then, the second polarization plate 22 is disposed so that the polarization axis has a relationship with the Y-axis direction, that is, the first polarization plate 21 giving crossed Nicols. In this state, measurement light is emitted from the light source 10, and a light signal detected by the light detector 50 in a state in which the phase modulation element 30 is driven is stored in the first waveform memory 81. This stored data is referred to as Ip(t) (S101).

Then, the sample 40 is installed in the optical path in place of the second polarization plate 22 by the exchange mechanism 90. In this state, measurement light is emitted from the light source 10, and the light signal detected by the light detector 50 in a state in which the phase modulation element 30 is driven is stored in the second waveform memory 82. The stored data is referred to as Is(t) (S102).

Here, the data Ip(t) recorded in step S01 is converted into data δ(t) of the phase change amount with respect to time using Equation (22) below.

[Math. 18]

$$\delta(t) = \cos^{-1}\left(1 - \frac{2I_p(t)}{I_m}\right) \quad (22)$$

According to Equation (22) above, it is seen only that the sign of δ varies according to time. Specifically, since the phase change amount varies according to a synchronization signal from the phase modulation element driver 31, positive or negative is discriminated between on the basis of a sign of the synchronization signal.

Figure 5:
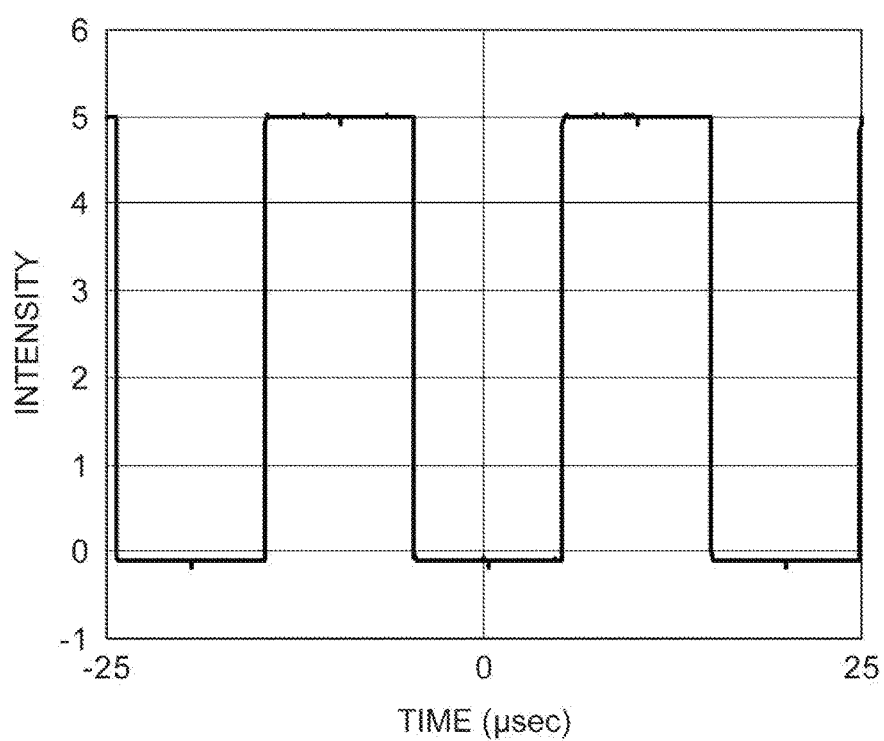
FIG. 5 is a diagram illustrating a waveform of a synchronization signal from a phase modulation element driver.
Figure 6:
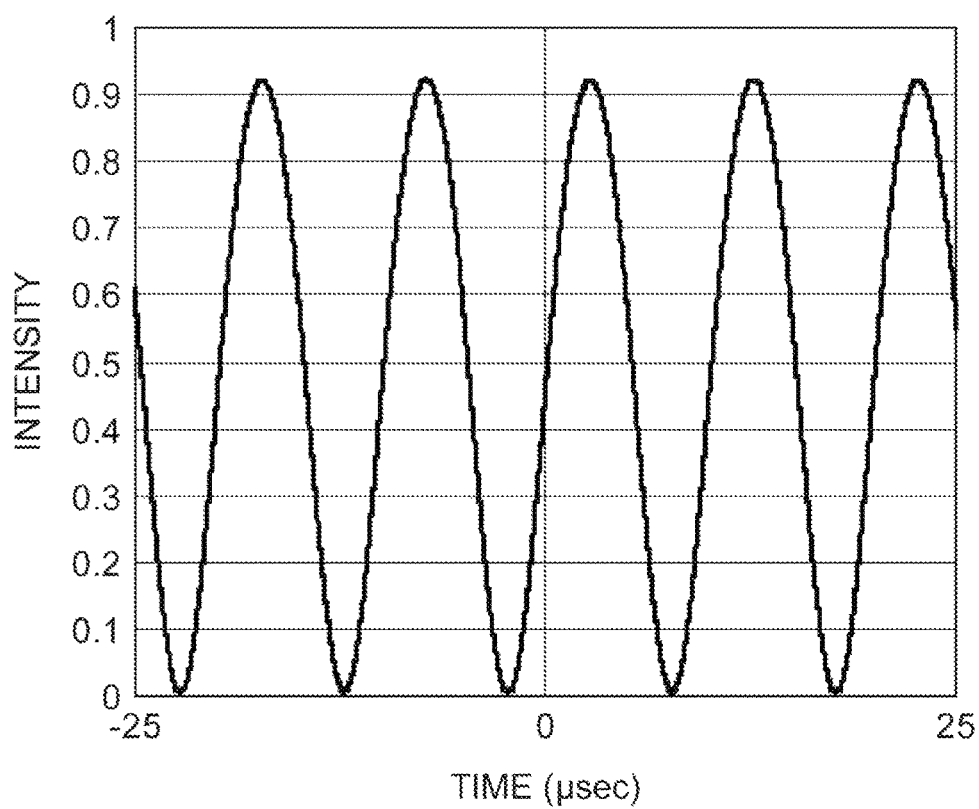
FIG. 6 illustrates data Ip(t) measured using a circular dichroism measuring device using a CaF2 PEM.

A specific method of calculating δ will be described with reference to FIGS. 5 and 6. FIG. 5 is a diagram illustrating a waveform of an actually measured synchronous signal from the phase modulation element driver 31. Further, FIG. 6 illustrates data Ip(t) measured using the circular dichroism measuring device 2 that uses a CaF2 PEM as the phase modulation element 30.

Here, an absolute value of δ can be obtained by adapting Equation (12) described above to a value at each time in FIG. 6. For a sign of δ, in FIG. 5, δ is positive in a time domain in which the synchronization signal is at a high level (with intensity α), and δ is negative in a time domain in which the synchronization signal is at a low level (with less than intensity 0). Data δ(t) of the phase change amount in the circular dichroism measuring device 2 using a CaF$_2$ PEM obtained actually in the above operation is illustrated in FIG. 7 (S103).

Figure 7:
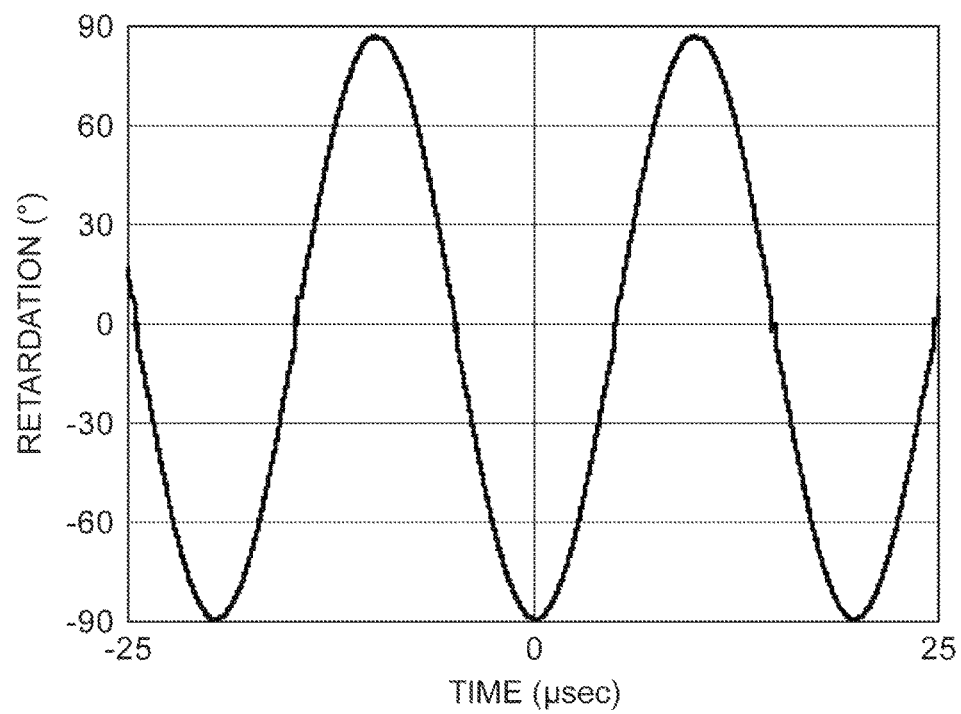
FIG. 7 illustrates data δ(t) of a phase change amount in the circular dichroism measuring device using the CaF2 PEM.

A phase amount at a time t of the measurement data Is(t) of the sample, that is, Is(δ) is obtained from the data δ(t) of the phase change amount illustrated in FIG. 7 (S104). Then, it is possible to directly obtain S00, S02, and S03 in the Mueller matrix according to the sample by performing curve fitting on a relationship of Is(δ) using the function shown in Equation (18) above (S105).

Hereinafter, effects obtained by using the circular dichroism measuring method according to this embodiment will be described while comparing with a method of the related art.

The sample 40 was rotated around the Z-axis from 0° to 90° with an increment of 15°, and dependence of S02 and S03 on an angle of rotation was evaluated. S03 that is a linear dichroism (LD) term greatly depends on the rotational angle, but if the circular dichroism measuring device has an ideal configuration, S02 is estimated not to depend on the rotational angle.

Figure 8:
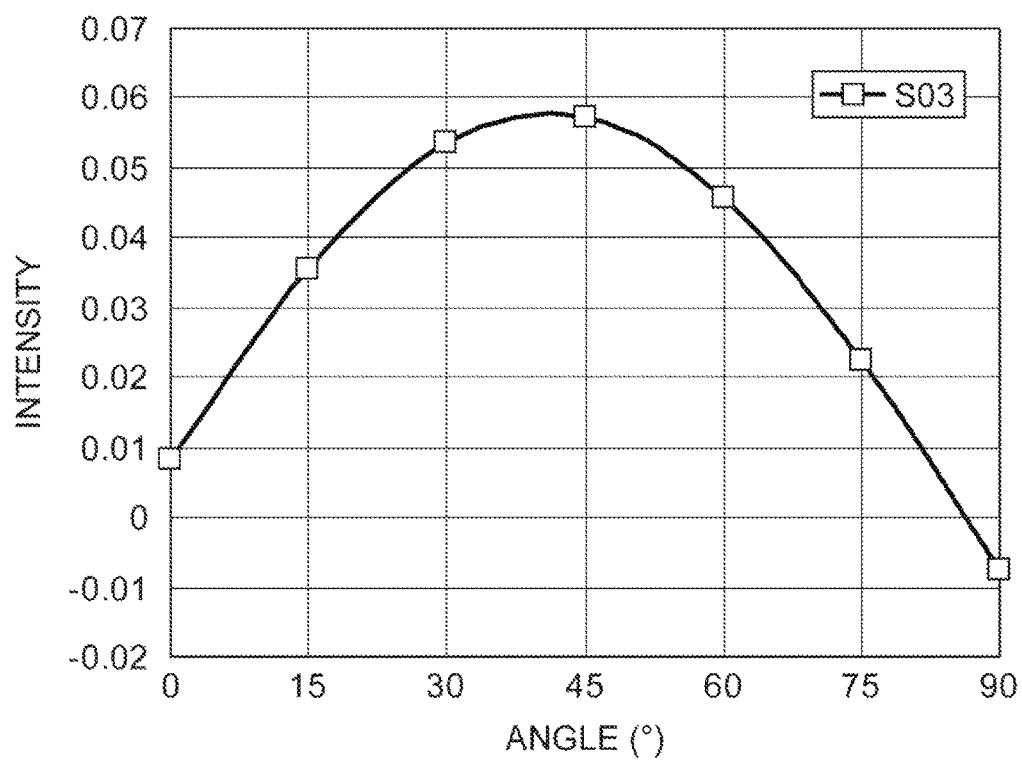
FIG. 8 is a diagram illustrating dependence of an S03 value on a rotational angle obtained using a method of the related art based on Is(t).
Figure 9:
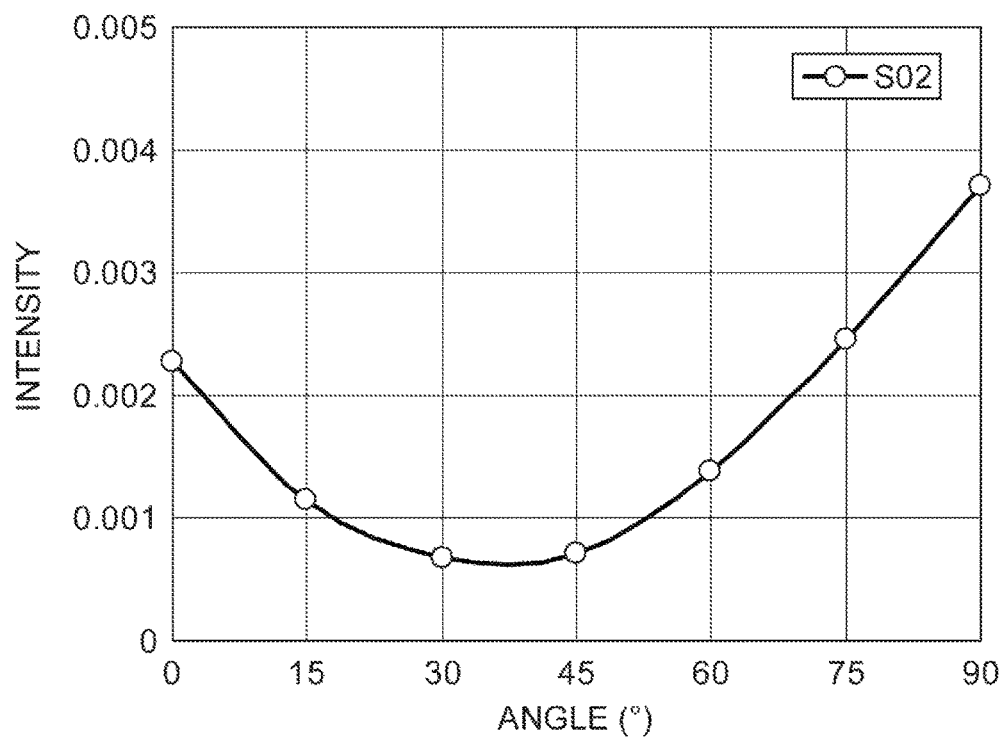
FIG. 9 is a diagram illustrating dependence of an S02 value on a rotational angle obtained using a method of the related art based on Is(t).

The dependence of the S03 value on the rotational angle obtained using a method of the related art, that is, a method of extracting an angular frequency component through FFT from Is(t) using a CaF$_2$ PEM as the phase modulation element 30, similar to the above embodiment, is illustrated in FIG. 8. Further, the dependence of the S02 value on the rotational angle is illustrated in FIG. 9. As illustrated in FIG. 7, in the CaF$_2$ PEM, it can be seen that the phase change amount does not exactly reach 90° and the CaF2 PEM used in this embodiment has residual distortion. In the case of such a PEM, S03, that is, a LD component is incorporated into S02, and great dependence on the rotational angle appears, as shown in Equation (21). In FIG. 9 illustrating actually measured S02, great dependence on the rotational angle is also illustrated. As described above, when the circular dichroism measuring device has an ideal configuration, it can be seen that S02 is greatly influenced by a distortion component of the PEM since S02 does not depend on the rotational angle.

Figure 10:
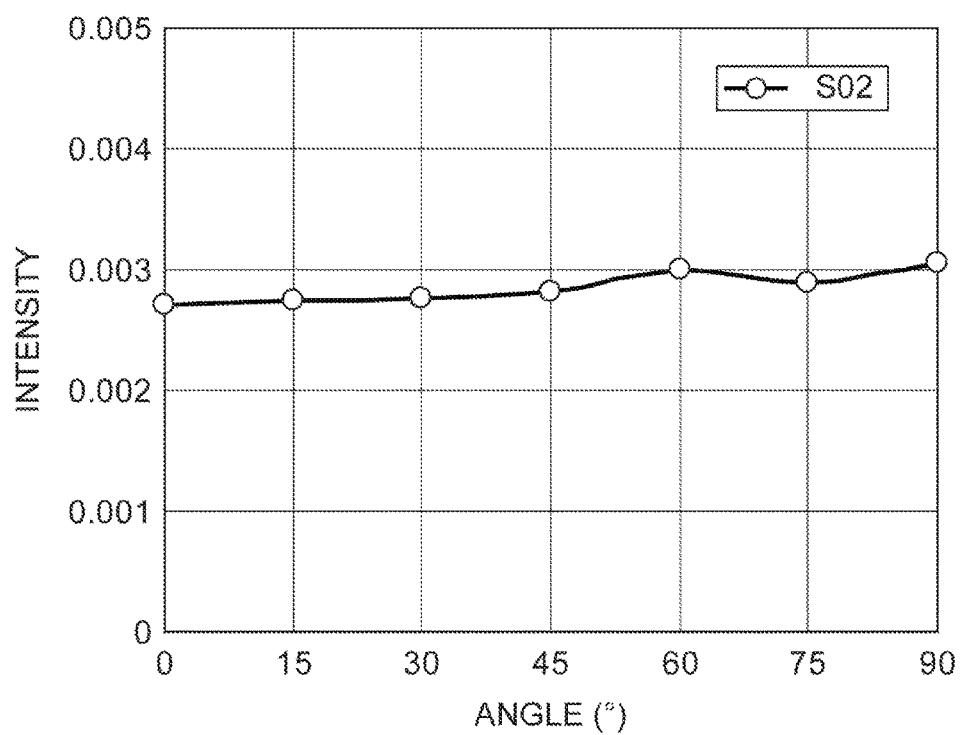
FIG. 10 is a diagram illustrating a value of S02 measured using a method of the related art using a PEM-100/IFS50 model made of quartz as a phase modulation element.

FIG. 10 illustrates a value of S02 measured by a method of the related art using a PEM-100/IFS50 model made of quartz as the phase modulation element 30. Since the PEM made of quartz has substantially no residual distortion, even when a circular dichroism measuring method according to the method of the related art is applied, there is no problem of residual distortion. Actually, FIG. 10 illustrates that rotational angle dependence of S02 is very small.

Figure 11:
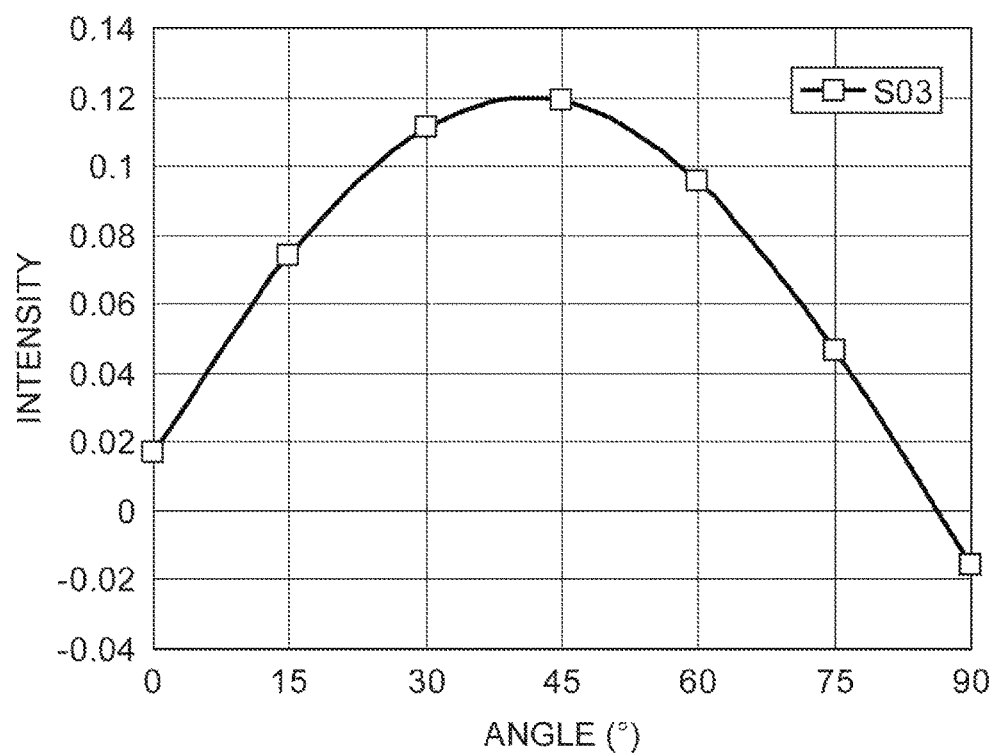
FIG. 11 is a diagram illustrating dependence of an S03 value on a rotational angle calculated according to a circular dichroism measuring method of this embodiment using a $CaF_2$ PEM as a phase modulation element.
Figure 12:
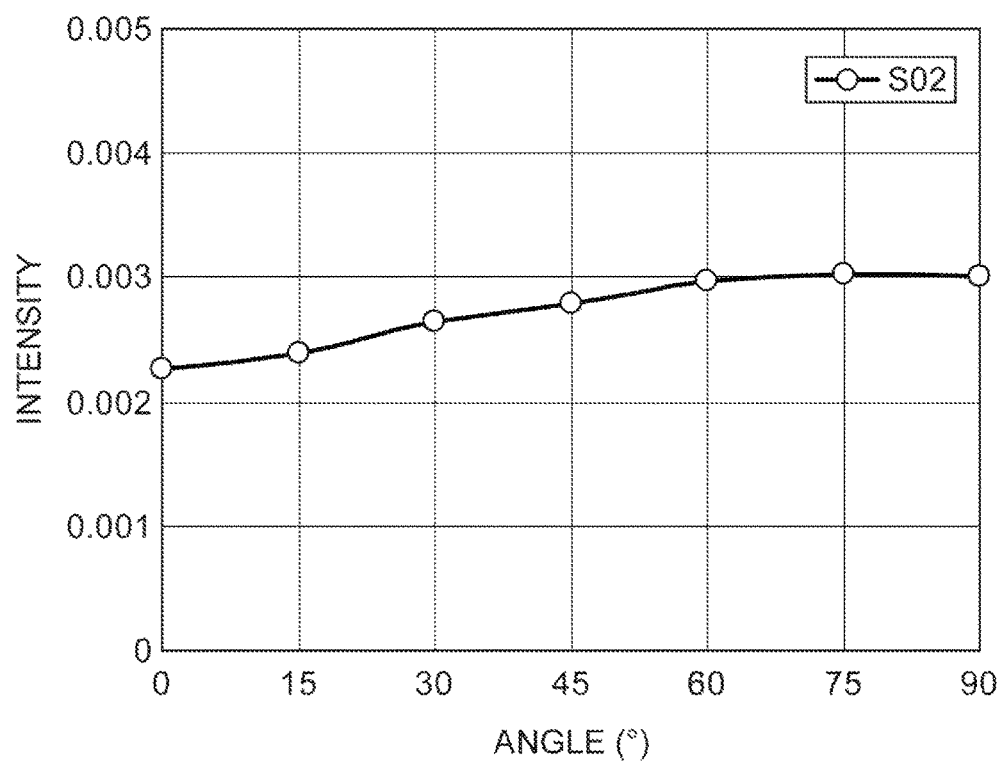
FIG. 12 is a diagram illustrating dependence of an S02 value on a rotational angle calculated according to a circular dichroism measuring method of this embodiment using a $CaF_2$ PEM as a phase modulation element.

Next, a case in which the circular dichroism measuring method according to an embodiment of the present invention is used will be described. Rotational angle dependence of an S03 value calculated according to the circular dichroism measuring method of this embodiment illustrated in FIG. 4 using a CaF$_2$ PEM as the phase modulation element 30 is illustrated in FIG. 11. Similarly, the rotational angle dependence of the S02 value is illustrated in FIG. 12. According to FIGS. 11 and 12, the rotational angle dependence can be confirmed only in S03 (FIG. 11), and an influence of S03, that is, a linear dichroism (LD) component is not observed in S02 (FIG. 12).

The above result shows that the same data as in a quartz PEM having no residual distortion, that is, the measurement data not greatly influenced by the distortion component is obtained from the CaF$_2$ PEM having residual distortion by applying the circular dichroism measuring method according to the present invention.

A phase difference amount is obtained from the obtained light intensity by inserting the PEM (phase modulation element 30) between the polarization plates (the first polarization plate 21 and the second polarization plate 22) set in the crossed Nicols described above in the above embodiment, but this does not preclude further use of an advanced phase difference measuring method.

(Second Embodiment)

Next, a second embodiment will be described using a device illustrated in FIG. 13. Repeated description of portions described in the first embodiment will be avoided and different portions will be described in detail.

Figure 13:
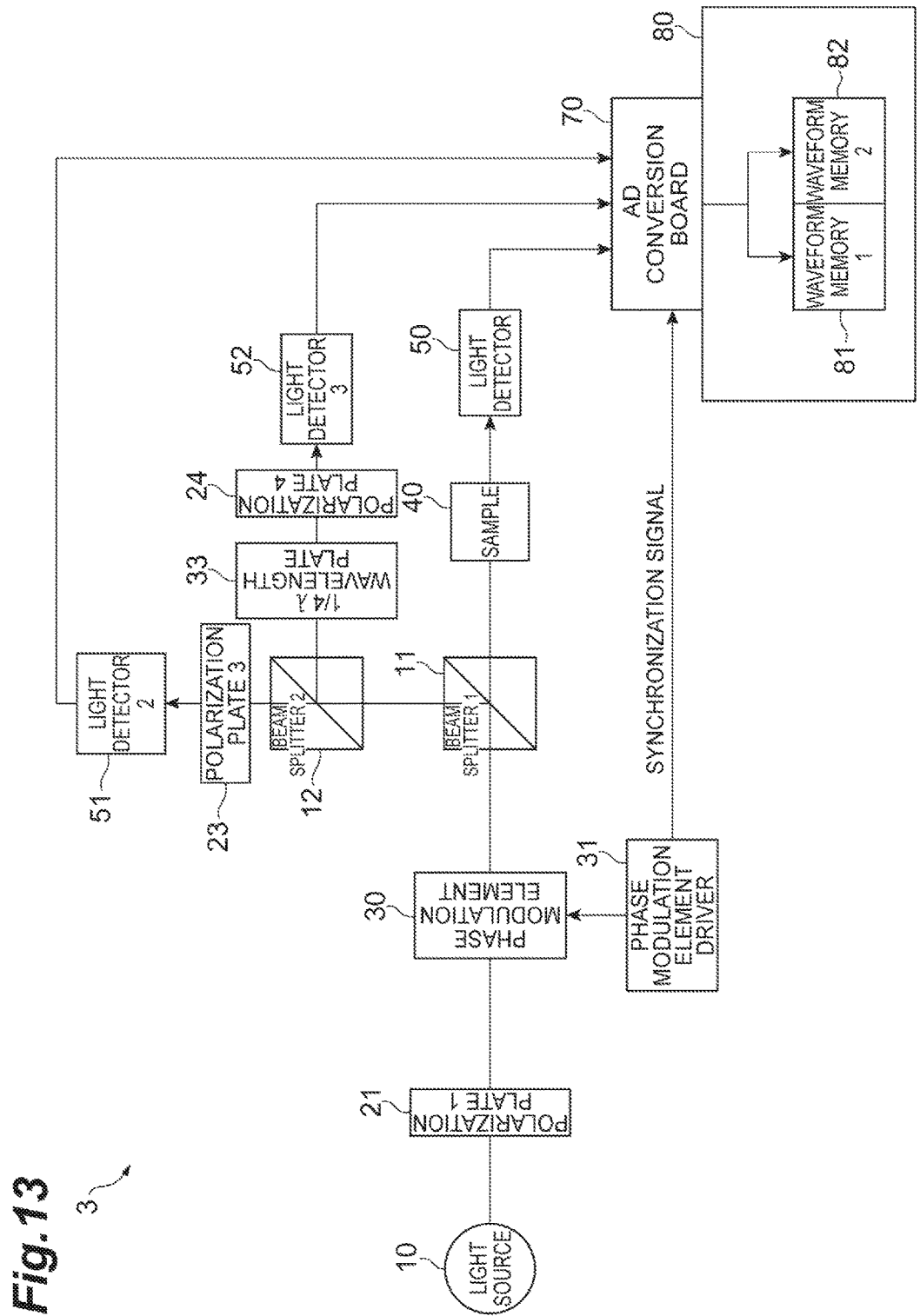
FIG. 13 is a diagram illustrating a schematic configuration of a circular dichroism measuring device according to a second embodiment.

The circular dichroism measuring device 2 shown in the first embodiment performs a plurality of measurements in order to obtain Im, Is(t), and Ip(t) required to obtain Is(δ), whereas a circular dichroism measuring device 3 illustrated in FIG. 13 has a configuration aiming at acquiring information necessary for measurement of circular dichroism through one measurement. That is, Is(t) acquisition means and Ip(t) acquisition means are simultaneously realized using a beam splitter.

Specifically, in the circular dichroism measuring device 3 illustrated in FIG. 13, a first beam splitter 11 is disposed between the phase modulation element 30 and the sample 40 to split light in two before the sample 40 is irradiated with light transmitted through the phase modulation element 30. One of the split lights is transmitted through the sample 40, and then, converted into an electrical signal by a light detector 50. The other of the split lights is guided to a second beam splitter 12 and split into two lights.

One of the lights split in the second beam splitter 12 is transmitted through a third polarization plate 23 (polarization plate 3) and converted into an electrical signal by a second light detector 51 (light detector 2). In this case, the third polarization plate 23 is disposed so that a polarization axis thereof has a relationship with a Y-axis, that is, the first polarization plate 21 giving crossed Nicols. Further, the other of the lights split in the second beam splitter 12 is transmitted through a ¼λ wavelength plate 33 and a fourth polarization plate 24 (polarization plate 4), and then, converted into an electrical signal by a third light detector 52 (light detector 3). The fourth polarization plate 24 is disposed so that a polarization axis thereof has a relationship with the X-axis, that is, the first polarization plate 21 giving parallel Nicols. Further, a fast axis of the ¼λ wavelength plate 33 is set in a direction of 45° around a Z-axis with respect to the polarization axis of the first polarization plate 21.

As the first beam splitter 11 and the second beam splitter 12, a non-polarization type beam splitter should be used so that a change in a polarization state does not occur at the time of light splitting.

In the circular dichroism measuring device 3 having the above configuration, optical components provided on each optical path formed between the light source and the light detector are as follows. A number in parentheses indicates a rotational angle around the Z-axis from the X-axis.

(Optical path A) light source 10→first polarization plate 21 (0)→sample 40→light detector 50

(Optical path B) light source 10→first polarization plate 21 (0)→third polarization plate 23 (90)→second light detector 51

(Optical path C) light source 10→first polarization plate 21 (0)→¼λ wavelength plate 33 (45)→fourth polarization plate 24 (0)→third light detector 52

The electrical signal due to the light detected by the light detector 50, the second light detector 51, and the third light detector 52 is input to the AD conversion board 70 attached to the computer 80, converted into a digital signal, and then, assigned to and stored in the first waveform memory 81 and the second waveform memory 82. In this case, a relationship between the optical path and data obtained in the detector on the optical path is as follows.

(1) Using the optical path A, Is(t) is obtained from the signal obtained by the light detector 50 (that is, the optical path A is Is(t) acquisition means).

(2) Using the optical path B, Ip(t) is obtained from the signal obtained by the second light detector 51 (that is, the optical path B is Ip(t) acquisition means).

(3) Using the optical path C, Ir(t) is obtained from the signal obtained by the third light detector 52.

Here, for Ir, if the light intensity measured in the third light detector 52 is analyzed using a Mueller matrix method, Equation (23) below is obtained. A relationship obtained in Equation (23) is illustrated in FIG. 14.

[Math. 19]

$$\frac{Ir(t)}{I_m} = \frac{1}{2}\{1 - \sin(\omega t + \alpha)\} \quad (23)$$

Figure 14:
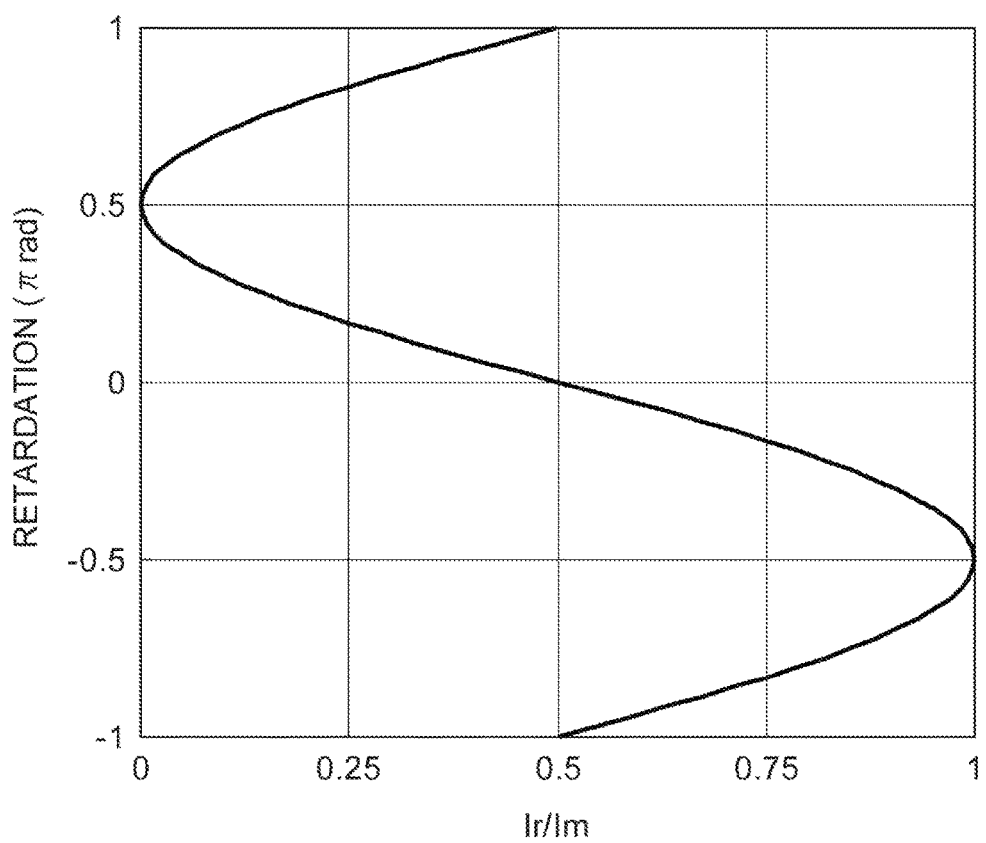
FIG. 14 is a diagram illustrating a relationship obtained using Equation (23).

According to FIG. 14, when Ir/Im is equal to or greater than 0.5, a retardation amount is negative, and when Ir/Im is equal to or smaller than 0.5, the retardation amount is positive. Therefore, Equation (22) is applied to Ip(t) to calculate an absolute value of δ(t), and a sign of δ(t) is determined according to whether Ir(t)/Im is smaller or greater than 0.5. Accordingly, the data δ(t) of the phase change amount can be obtained.

It is possible to obtain the phase amount at a time t of the measurement value Is(t) of the sample, that is, Is(δ) on the basis of the data δ(t) of the phase change amount obtained as above and Is(t) obtained from the measurement in the optical path A, similar to the first embodiment. S00, S02, and S03 in the Mueller matrix are directly obtained by performing curve fitting on a relationship of Is(δ) using the function shown in Equation (18).

Thus, when the circular dichroism measuring device 3 according to the second embodiment is used, it is possible to perform the circular dichroism measurement using the same steps S103 to S105 as in the circular dichroism measuring method according to the first embodiment illustrated in FIG. 4. For steps S101 and S102, it is possible to use the measurement based on the optical path A and the measurement based on the optical path B in the circular dichroism measuring device 3 according to the second embodiment.

That is, in the circular dichroism measuring device 3 according to the second embodiment, the replacement between the sample 40 and the second polarization plate 22 as in the circular dichroism measuring device 2 according to the first embodiment is not necessary, and it is possible to acquire the retardation (phase difference) of the phase modulation element in real time. Thus, for example, even when a phase modulation element with significant temperature characteristics or drift characteristics, such as a liquid crystal phase modulation element, is used, it is possible to obtain optical constants such as S00, S02, and S03 with good accuracy. Accordingly, it is possible to perform high-accuracy circular dichroism measurement.

The embodiments of the present invention have been described above, but the present invention is not limited to the above embodiments and various changes can be performed.

REFERENCE SIGNS LIST 1 to 3: Circular dichroism measuring device
10: Light source
20 to 24: Polarization plate
30: Phase modulation element
31: Phase modulation element driver
40: Sample
50 to 52: Light detector
60: Lock-in amplifier
70: AD conversion board
80: Computer
81, 82: Waveform memory

The invention claimed is:
1. A circular dichroism measuring method in a circular dichroism measuring device including a light source, a polarization plate that extracts linearly polarized light from light emitted from the light source, a phase modulation element that modulates the linearly polarized light, and a light detector that detects light modulated by the phase modulation element and then transmitted through a sample, the circular dichroism measuring method comprising:
a sample data acquisition step of acquiring a change in a light intensity with respect to time in the light detector;

a phase amount change acquisition step of acquiring a change in a phase amount with respect to time of the phase modulation element; and an analysis step of converting the change in light intensity acquired in the sample data acquisition step into a change with respect to the phase amount on the basis of the change in the phase amount acquired in the phase amount change acquisition step, and calculating matrix elements S00, S02, and S03 when a Mueller matrix according to the sample is as shown in Equation (1) below on the basis of the change with respect to the phase amount:

$$S = S(\theta) = e^{-Av} \cdot \begin{pmatrix} S00 & S01 & S02 & S03 \\ S10 & S11 & S12 & S13 \\ S20 & S21 & S22 & S23 \\ S30 & S31 & S32 & S33 \end{pmatrix}. \quad (1)$$

2. The circular dichroism measuring method according to claim 1, wherein the phase amount change acquisition step includes acquiring data Is(t) indicating a temporal change in a light signal detected by the light detector by emitting light from the light source in a state in which the sample is disposed, and the phase amount change acquisition step includes:

a step of acquiring data Ip(t) indicating a temporal change in a light signal detected in the light detector by emitting light from the light source in a state in which a second polarization plate having a relationship with the polarization plate giving crossed Nicols is disposed on an optical path from the light source, in place of the sample; and the analysis step includes:

a step of converting the data Ip(t) into data δ(t) indicating a temporal change of the phase change amount due to the phase modulation element using Equation (2) below, $$\delta(t) = \cos^{-1}\left(1 - \frac{2I_P(t)}{I_m}\right); \quad (2)$$

an Is(δ) calculation step of calculating data Is(δ) according to the phase amount at time t of data Is(t) of the sample on the basis of the data δ(t) of the phase change amount; and a matrix element calculation step of performing fitting on the data Is(δ) using Equation (3) below to calculate matrix elements S00, S02, and S03 in the Mueller matrix according to the sample:

$$I = \frac{1}{2}e^{-Av} \cdot (S00 + S03\cos\delta - S02\sin\delta). \quad (3)$$

* * * * *